US011110449B2

(12) United States Patent
Ranade et al.

(10) Patent No.: US 11,110,449 B2
(45) Date of Patent: Sep. 7, 2021

(54) PROCESS FOR RECOVERY AND REGENERATION OF DEACTIVATED CATALYSTS USED IN DIALKYL CARBONATE SYNTHESIS

(71) Applicant: COUNCIL OF SCIENTIFIC AND INDUSTRIAL RESEARCH, New Delhi (IN)

(72) Inventors: Vivek Vinayak Ranade, Pune (IN); Ashutosh Anant Kelkar, Pune (IN); Vilas Hari Rane, Pune (IN); Anil Kisan Kinage, Pune (IN); Savita Kiran Shingote, Pune (IN); Lalita Sanjib Roy, Pune (IN); Dhananjay Ravindra Mote, Pune (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 315 days.

(21) Appl. No.: 15/562,044

(22) PCT Filed: Mar. 23, 2016

(86) PCT No.: PCT/IN2016/050094
§ 371 (c)(1),
(2) Date: Sep. 27, 2017

(87) PCT Pub. No.: WO2016/157218
PCT Pub. Date: Oct. 6, 2016

(65) Prior Publication Data
US 2018/0104680 A1  Apr. 19, 2018

(30) Foreign Application Priority Data

Mar. 27, 2015  (IN) .................... IN0849/DEL/2015

(51) Int. Cl.
*B01J 38/62* (2006.01)
*B01J 38/66* (2006.01)
(Continued)

(52) U.S. Cl.
CPC .............. *B01J 38/62* (2013.01); *B01J 23/10* (2013.01); *B01J 23/92* (2013.01); *B01J 38/02* (2013.01);
(Continued)

(58) Field of Classification Search
CPC ... B01J 38/62; B01J 38/02; B01J 38/68; B01J 38/60; B01J 38/66; B01J 23/10;
(Continued)

(56) References Cited

U.S. PATENT DOCUMENTS 3,149,149 A  9/1964 Gorman et al.
3,806,589 A  4/1974 Becher et al.
(Continued)

FOREIGN PATENT DOCUMENTS

JP  S60122718 A  7/1985
WO  00/37416 A1  6/2000
(Continued)

OTHER PUBLICATIONS

Kobayashi et al. "Rare-Earth Metal Triflates in Organic Synthesis", Chem. Rev. 2002, 102, 2227-2302 (Year: 2002).*
(Continued)

*Primary Examiner* — Anthony J Zimmer
*Assistant Examiner* — Syed T Iqbal
(74) *Attorney, Agent, or Firm* — BakerHostetler

(57) ABSTRACT

The present invention discloses a process for recovery and regeneration of rare earth metals or salts thereof used as catalyst and which is conveniently integrated within the overall flow sheets of manufacturing dialkyl carbonates. Alkyl carbamate, alcohol and a rare earth metal salt as
(Continued)

catalyst selected from the lanthanide series are added in a reactor to afford dialkyl carbonate. The rare earth metal catalyst is selected from samarium, cerium, lanthanum, neodymium, ytterbium, europium and gadolinium. Ammonia is added to a portion of the reaction mixture to precipitate the catalyst and the separated deactivated catalyst is dissolved in acid to afford regenerated catalyst, e.g., in triflic acid in the case of samarium triflate catalyst.

8 Claims, 1 Drawing Sheet

(51) Int. Cl.
| | |
|---|---|
| *B01J 38/68* | (2006.01) |
| *B01J 23/10* | (2006.01) |
| *B01J 23/92* | (2006.01) |
| *C07C 68/00* | (2020.01) |
| *B01J 38/60* | (2006.01) |
| *B01J 38/02* | (2006.01) |
| *C07C 69/96* | (2006.01) |

(52) U.S. Cl.
CPC ............. *B01J 38/60* (2013.01); *B01J 38/66* (2013.01); *B01J 38/68* (2013.01); *C07C 68/00* (2013.01); *C07C 69/96* (2013.01); *Y02P 20/584* (2015.11)

(58) Field of Classification Search
CPC .......... B01J 23/92; C07C 69/96; C07C 68/00; Y02P 20/584
See application file for complete search history.

(56) References Cited

U.S. PATENT DOCUMENTS

| | | |
|---|---|---|
| 5,132,259 A | 7/1992 | Curnutt |
| 2011/0045965 A1 | 2/2011 | Ryu |
| 2012/0156116 A1* | 6/2012 | Gao .......................... C22B 3/44 423/21.1 |
| 2014/0051880 A1* | 2/2014 | Baik ....................... C07C 68/00 558/277 |

FOREIGN PATENT DOCUMENTS

| | | |
|---|---|---|
| WO | 2013130170 A1 | 9/2013 |
| WO | 2014072803 A1 | 5/2014 |
| WO | WO-2014072803 A1 * | 5/2014 ............. C07C 68/00 |

OTHER PUBLICATIONS

P. Wang et al., "Two-Step Synthesis of Dimethyl Carbonate from Urea, Ethylene Glycol and Methanol using Acid-Base Bifunctional Zinc-Yttrium Oxides", Fuel Processing Technology, 2014, vol. 25, pp. 359-365.

* cited by examiner

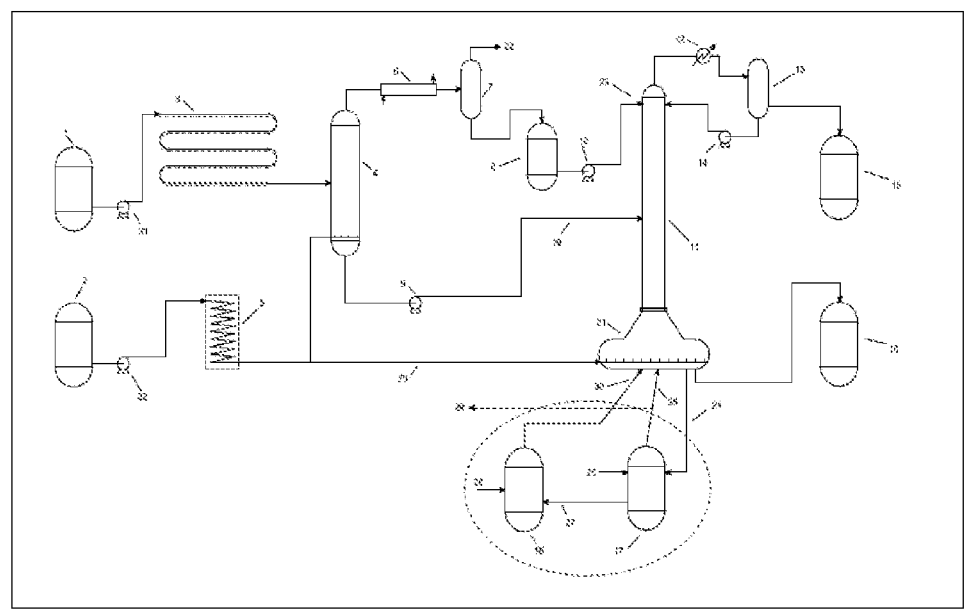

ously, part of the catalysts may precipitate during the course of the reaction. Precipitation of the catalysts leads to reduction in activity and selectivity towards dialkyl carbonates. In order to develop a stable process for manufacturing dialkyl carbonates, it is essential to resolve and address this problem of catalyst precipitation. One of the ways is to develop a process for the recovery/regeneration of the catalyst which is disclosed in this invention.

PROCESS FOR RECOVERY AND REGENERATION OF DEACTIVATED CATALYSTS USED IN DIALKYL CARBONATE SYNTHESIS

CROSS REFERENCE TO RELATED APPLICATIONS

This application is a National Stage of International Application No. PCT/IN2016/050094, filed on Mar. 23, 2016, which claims priority to Indian patent application no. 0849/DEL/2015, filed on Mar. 27, 2015, the disclosures of which are incorporated by reference in their entirety.

FIELD OF THE INVENTION

The present invention relates to a process for the recovery and regeneration of deactivated catalysts. More particularly, the present invention relates to a process for recovery and regeneration of rare earth metals or salts thereof used as catalysts for synthesis of dialkyl carbonates.

BACKGROUND AND PRIOR ART

Dimethyl carbonate (DMC) is an important intermediate and is widely used in industry. Owing to its low toxicity, dimethyl carbonate is considered a "green" chemical product with bright development prospects. This increasing focus is mainly due to the bio-degradability, with a low bioaccumulation as well as its low toxicity. Significant amount of work is being carried out to develop environmentally safer routes for the synthesis of DMC. Besides diethyl carbonate, other dialkyl carbonates like diethyl, dipropyl and dibutyl carbonate also find several applications.

The inventors hold patent applications for the synthesis of dimethyl carbonate and other dialkyl carbonates using rare earth metal salts (nitrates, methyl sulfonate, trifluoromethyl sulfonate, chloride etc) as homogeneous catalysts. These homogeneous catalysts offer excellent activity and selectivity towards desired dialkly carbonates. However, part of the catalysts may precipitate during the course of the reaction. Precipitation of the catalysts leads to reduction in activity and selectivity towards dialkyl carbonates. In order to develop a stable process for manufacturing dialkyl carbonates, it is essential to resolve and address this problem of catalyst precipitation. One of the ways is to develop a process for the recovery/regeneration of the catalyst which is disclosed in this invention.

Recovery or regeneration of catalysts also contributes towards the economics of the process. A process for recovery or regeneration of catalyst which provides a catalyst that performs as good as a neat or fresh catalyst is only additionally advantageous towards the economics of the process.

WO 2014/072803 A1 (COUNCIL SCI ENT IND RES [IN]) 15 May 2014 (2014-05-15) page 15, line 12—page 19, line 13; tables 1b,2a,2b disclosed synthesis of methyl carbamate (MC) and dimethyl carabonate (DMC) in the presence of stripping inert gas or superheated methanol vapors using a packed column reactor and bubble column reactor.

Article titled "A novel catalyst for transesterification of dimethyl carbonate with phenol to diphenyl carbonate: samarium trifluoromethanesulfonate" by M Fuming et al. published in Journal of Molecular Catalysis A: Chemical, 2002, 184 (1-2), pp 465-468 reports a novel catalyst for synthesis of diphenyl carbonate (DPC) by transesterification of dimethyl carbonate (DMC) with phenol. This catalyst could work in aqueous media and in air, and proved reusable. From the data in results, it was found that the catalytic activities of the recovered catalyst are almost the same as that of fresh catalyst.

U.S. Pat. No. 5,132,259 disclosed method for reactivating the supported heterogeneous catalyst used in the aforementioned carbonylation reaction. The regeneration method comprises drying and contacting the catalyst with a gaseous stream of hydrogen halide for a period of time which is sufficient to convert all of the metal present in whatever form to the corresponding metal halide. This regeneration process unexpectedly allows the carbonylation catalyst to be treated under strongly acidic conditions without adversely affecting the performance and selectivity of the catalyst.

PCT application no. 2013130170 disclosed a method of preparing a dialkyl carbonate and diol products in an integrated process comprising:

(a) reacting an alkylene oxide with carbon dioxide in the presence of a halide-containing homogeneous carbonation catalyst in a first reaction zone to form a crude cyclic carbonate product, the crude cyclic carbonate product containing amounts of the carbonation catalyst;

(b) introducing the crude cyclic carbonate product from the first reaction zone along with an aliphatic monohydric alcohol to a second reaction zone containing a transesterification catalyst comprised of an ion exchange resin and allowing the cyclic carbonate product and monohydric alcohol to react under reaction conditions to form the dialkyl carbonate and diol products until the ion exchange resin catalyst has deactivated to a selected degree; and (c) regenerating the deactivated ion exchange resin of the second reaction zone by washing the ion exchange resin with water and contacting the washed ion exchange resin with a regeneration solution containing regenerating ions before continuing step (b).

US patent application no. 20110045965 disclosed a process for reactivating a spent solid alcoholysis catalyst, the process comprising: removing polymeric materials deposited on the catalyst; and re-depositing catalytically active metals on the solid catalyst, wherein the removing and re-depositing are performed in situ in a transesterification reactor.

PCT application no. 2000037416 disclosed a method for reclaiming metal catalyst species from a metal-containing aqueous extract stream from diaryl carbonate production mixtures, comprising treating a metal-containing aqueous extract stream of a mixture from the production of diaryl carbonates with a first portion of a precipitating agent effective to precipitate at least one first metal catalyst species from the extract, wherein the precipitating agent is selected from the group consisting of acetylacetone, oxalic acid, salts of acetylacetonates and salts of oxalates.

U.S. Pat. No. 3,149,149 disclosed a process for the production of acrylonitrile by the catalytic reaction of acetylene and hydrogen cyanide. Further, they disclosed an improvement in the recovery of catalyst used in the reaction. Still more particularly, it relates to a method for regenerating the copper values from a deactivated or spent catalyst solution employed in the reaction.

U.S. Pat. No. 3,806,589 disclosed a process for the recovery of antimony halides as substantially pure antimony (Ill) chloride from a spent antimony halide catalyst that had been used in a process for the fluorination of a halogenated hydrocarbon with hydrogen fluoride which catalysts normally consist essentially of a mixture of antimony (Ill) and antimony (V) halides and include compounds which dissociate to yield fluoride ions and compounds which dissociate to yield ions of heavy metals.

Article titled "The effects of promoters on catalytic properties and deactivation-regeneration of the catalyst in the synthesis of dimethyl carbonate" by J Ruixia et al. published in Applied Catalysis A: General, 2003, 238 (1), pp 131-139 reports the effects of different alkali metal promoters in $PdCl_2$—$CuCl_2$/activated carbon (a.c.) catalyst on the reaction performance for synthesizing dimethyl carbonate (DMC) by gas-phase oxidative carbonylation of methanol. The catalytic activity after two times of regeneration can still be restored to 93% of the fresh catalyst. The run time of this catalyst is up to 300 h.

There are no reports on the reactivation and regeneration of spent homogeneous catalysts for DMC or other dialkyl carbonate synthesis. Further, there are no reports on the recovery/regeneration of homogeneous catalysts based on rare earth metal salts for the synthesis of DMC from/methyl carbamate. Therefore there is need to develop a process for the recovery and regeneration of rare earth metal salts based catalysts used in the dialkyl carbonate synthesis.

OBJECTIVE OF THE INVENTION

The main objective of the present invention is to provide a process for the recovery and regeneration of rare earth metals or salts thereof which are employed as catalysts in the process of synthesis of dialkyl carbonates.

Another objective of present invention is to provide a process for the recovery and regeneration of rare earth metals or salts thereof which are employed as catalysts for the process of synthesis of dimethyl carbonate.

SUMMARY OF THE INVENTION

Accordingly, the present invention provides a process for recovery and regeneration of catalyst used in the synthesis of dialkyl carbonates comprising the steps of:
  a) adding alkyl carbamate, alcohol and rare earth metal salt as catalyst selected from lanthanide series in a reactor to afford corresponding dialkyl carbonate and reaction mixture with deactivated catalyst;
  b) removing part of reaction mixture of step (a) from the reactor bottom;
  c) Separating deactivated catalyst residue from the reaction mixture of step (b) and dissolving in acid corresponding to the rare earth metal salt to afford regenerated catalyst.

In one embodiment, said process optionally comprises addition of ammonia to the part of reaction mixture of step (b) in the pressure range of 1 to 25 bar and temperature ranging from 60 to 200° C. to precipitate catalyst.

In preferred embodiment, said dialkyl carbonate is selected from di methyl carbonate, di ethyl carbonate, di propyl carbonate, di butyl carbonate and such like.

In another preferred embodiment, said rare earth metal is selected from Samarium (Sm), Cerium (Ce), Lanthanum (La), Neodymium (Nd), Ytterbium (Yb), Europium (Eu) and Gadolinium (Gd).

In yet another preferred embodiment, said salts of rare earth metal ise selected from methane sulphonate, triflate, nitrate, chloride and para toluene sulphonate.

In still another preferred embodiment, said dialkyl carbonate is di methyl carbonate and said rare earth metal salt catalyst is samarium trifluoromethanesulfonate.

In yet still another preferred embodiment, said acid for re-dissolving of precipitate is selected from the methane sulphonic acid, trifluoromethanesulfonic acid, nitric acid, para toluene sulfonic acid and hydrochloric acid.

BRIEF DESCRIPTION OF FIGURES

FIG. 1: Schematic showing the process of synthesis of dialkyl carbonates. The portion encircled with dotted line shows the portion of the reactor that recovers/regenerates the catalyst.

[Urea+Alcohol feed vessel (1), pump (9, 10, 14, 31), Tubular reactor (3), Alcohol storage vessel (2), heater (5), superheated alcohol (stream 20), stripper (4), Dialkyl carbonate reactor (11), cooler (6), Liquid phase from vessel (7), product storage vessel (16), condenser (12), flash vessel (13) storage vessel (15), reactor contents stream (stream 24), ammonia stream (stream 25), filtration/precipitation vessel (17),
liquid phase stream (stream 26), solid phase slurry (stream 27), Regeneration vessel (18), acid stream (stream 28), regenerated catalyst stream (stream 30), liquid phase a purge stream (stream 29)]

DETAILED DESCRIPTION OF THE INVENTION

The invention will now be described in detail in connection with certain preferred and optional embodiments, so that various aspects thereof may be more fully understood and appreciated.

In the view of above, the present invention provides a process for the recovery and regeneration of rare earth metals or salts thereof which are employed as catalysts for the process of synthesis of dialkyl carbonates.

A novel process to re-dissolve the precipitated catalyst to restore activity and selectivity towards desired products is disclosed. The re-dissolved catalyst is shown to realize activity similar to the original fresh catalyst.

In an embodiment, the present invention provides a process for recovery and regeneration of catalyst used in the synthesis of dialkyl carbonates comprising the steps of:
  a) adding alkyl carbamate, alcohol and rare earth metal salt as catalyst selected from lanthanide series in a reactor to afford corresponding dialkyl carbonate and a reaction mixture with deactivated catalyst;
  b) removing part of reaction mixture of step (a) from the reactor bottom;
  c) Separating deactivated catalyst residue from the reaction mixture of step (b) and dissolving in acid corresponding to the rare earth metal salt to afford regenerated catalyst.

In one embodiment, said process optionally comprises addition of ammonia to the part of reaction mixture of step (b) in the pressure range of 1 to 25 bar and temperature ranging from 60 to 200° C. to precipitate catalyst.

In preferred embodiment, said alkyl carbamate is methyl carbamate and said alcohol is methanol.

In preferred embodiment, said dialkyl carbonates are selected from di methyl carbonate, di ethyl carbonate, di propyl carbonate, di butyl carbonate and such like.

In another preferred embodiment, said rare earth metals are selected from Samarium (Sm), Cerium (Ce), Lanthanum (La), Neodymium (Nd), Ytterbium (Yb), Europium (Eu) and Gadolinium (Gd).

In yet another preferred embodiment, said salts of rare earth metal is selected from methane sulphonate, triflate, nitrate, chloride and para toluene sulphonate.

In still another preferred embodiment, said dialkyl carbonate is di methyl carbonate and said rare earth metals salt catalyst is samarium trifluoromethanesulfonate.

In yet still another preferred embodiment, said acid for re-dissolving of precipitate is selected from the methane sulphonic acid, trifluoromethanesulfonic acid, nitric acid, para toluene sulfonic acid and hydrochloric acid.

In one embodiment, the present invention provides a process for the recovery and regeneration of samarium para toluene sulphonate which is employed as catalysts for the process of synthesis of dimethyl carbonates.

The salts of rare earth metals used as catalysts in the synthesis of dialkyl carbonates are recovered by a simple process comprising dissolution of precipitated catalyst in the liquid stream taken out of the reactor (FIG. 1) with acid (corresponding to the rare metal salt used as a catalyst), when the catalytic activity is diminished significantly over the period, the catalyst is precipitated by drawing the reaction mass out of the reactor and interacting the reaction mass with ammonia for a specified period (FIG. 1). The precipitate is separated and again dissolved with acid (corresponding to the rare metal salt used as a catalyst) to obtain rare earth metal salt. The solution thus obtained can be used as catalyst.

The recovered catalyst may be separated or may be used in solution to catalyze further cycles of the process.

The process of recovery of catalyst as disclosed herein retains the catalytic activity for the synthesis of dialkyl carbonates over at least two cycles.

The catalyst thus prepared from spent catalyst solution is found to possess activity substantially equivalent to the original catalysts. The recycled catalyst provides conversion of alkyl carbamate with high selectivity towards corresponding dialkyl carbonate equivalent to the experiment with the fresh catalyst.

The processes for regeneration and recovery of catalysts for the process of synthesis of dialkyl carbonates are conveniently integrated within the overall flow sheets of manufacturing dialkyl carbonates. The process offers a convenient way to establish and maintain consistent activity and selectivity towards desired dialkyl carbonates.

In the process for the synthesis of dialkyl carbonates, a stream of reacting mass is withdrawn from the reactor is processed through steps disclosed in this invention (FIG. 1, steps shown in dotted ellipse). The split stream is withdrawn from the reactor. It is optionally contacted with ammonia (as gas or as dissolved in methanol). The solids are filtered and fed to another vessel. The filtrate is recycled back to the reactor with or without a purge. The solids stream is contacted with appropriate acid containing stream to regenerate the catalyst. The regenerated catalyst is recycled back to the reactor with and without a purge.

From recycle experiments it is observed that $Sm(CF_3SO_3)_3$ precipitates after bubbling of $NH_3$ in initial reaction mixture. This precipitate is dissolved initially by $N_2$ stripping at 90° C. but the nature of precipitate changes after reaction and this precipitate could not be re-dissolved even after prolonged $N_2$ bubbling at reflux temperature. But on addition of triflic acid precipitate dissolves and original activity is regained. This indicates that precipitated catalyst is active in-situ with total amount of samarium distributed in solution and in precipitated catalyst without any loss in total Sm content.

The invention will now be explained with reference to specific examples and embodiments. They should not be construed to limit the scope of the invention in any way.

EXAMPLES

Example 1: Catalyst Recycle and Regeneration

Initially feed of (Methyl Carbamate(MC)+MeOH) and $Sm(CF_3SO_3)_3$ catalyst were charged into reactor and saturated with $NH_3$. The reactor was opened and it was observed that part of Sm precipitated out of the solution. Sample of supernatant liquid was taken for ICP analysis (Table 1). The reactor was closed again and was stripped with N2 to remove $NH_3$. At this point the reactor was opened to check the presence of precipitate. It was observed that after removal of excess ammonia precipitate was completely dissolved, indicating that the precipitation is reversible in nature. From the ICP analysis, it can be clearly seen that initial sample before passing $NH_3$ showed 0.682 g of Sm. After addition of $NH_3$, the amount of Sm in solution decreased from 0.682 g to 0.056 g indicating significant precipitation of Sm (Table 1 entry 2). In next step when N2 was purged through solution to drive off excess NH3; at this stage precipitate dissolved and samarium was restored to its original amount i.e 0.624 g in solution (Table 1 entry 3). The results clearly indicate that the precipitation is reversible in nature.

Similar experiment was repeated with Sm(NO3)3 as catalyst and the results are presented in Table 2. Here also reversibility of Sm precipitation was observed (Table 2a, entry 1, 2, 3). The reaction of DMC synthesis was carried out at 180° C. for 8 h using same reaction mixture (Table 2b). At the end of the reaction sample was analyzed by GC analysis and 52.5% conversion of MC with 73% selectivity DMC was obtained. Part of the catalyst was found to be precipitated in the solution. The reaction mixture was purged with nitrogen for 21 h, however, precipitate did not dissolve (Table 2b). This indicates that the nature of the precipitate is different and is not reversible as observed in the earlier experiment. There is a need to develop protocol for dissolution of the precipitate to generate active catalyst.

TABLE 1

ICP analysis of precipitation experiments
[2 litre reactor with $Sm(CF_3SO_3)_3$ catalyst]

| Entry | $Sm(CF_3SO_3)_3$ | Observation | Sm in (g) |
|---|---|---|---|
| 1 | Initial sample (MC + MeOH + catalyst) | Homogeneous mixture | 0.682 |
| 2 | After passing ammonia through initial sample | Precipitate formation | 0.056 |
| 3 | N2 stripping through precipitated catalyst solution | Precipitate dissolved | 0.624 |
| 4 | After 8 h of reaction | Precipitate formed again | 0.1418 |
| 5 | After 16 h of reaction | Precipitate retained | 0.1048 |
| 6 | After 24 h of reaction | Precipitate retained | 0.087 |
| 7 | After 24 h of reaction, g triflic acid was added | Precipitate dissolved | 0.663 |

TABLE 2

| | ICP analysis of precipitation experiments with Sm(NO3)3 in 2 L | |
|---|---|---|
| Entry | Description | Sm in Sm(NO$_3$)$_3$ by ICP |
| 1 | Sm (g) in Initial sample (MC + MeOH + catalyst) | 0.81 |
| 2 | Sm (g) in solution after NH3 addition (MC + MeOH + catalyst) | 0.22 |
| 3 | Sm (g) in solution after N2 stripping (MC + MeOH + catalyst) | 0.83 |

| Activity of Sm(NO$_3$)$_3$ catalyst | | | | |
|---|---|---|---|---|
| Entry | MC Conv (%) | DMC Sel (%) | MMC Sel (%) | Observation |
| 1 (std run) | 53 | 77 | 6 | Precipitate formed |
| 2 | 52.5 | 73 | 4.5 | Formed precipitate partly dissolved after N2 stripping for 21 h |

Reaction condition-MC:MeOH::1:1.5 Catalyst Sm(NO$_3$)$_3$ (3 g), N2 and MeOH stripping 7 ml/min, time 16 h, temperature 180° C., 2 L CSTR

Example 2: Recycle Experiment

Example 2a: Standard Run

Methyl carbamate (MC) 228 g (304 mmol) and methanol 146 g (4562 mmol) with 3 g of Sm(CF3SO3)$_3$ were charged to a 2000 ml reactor connected to a nitrogen reservoir from gas inlet valve. The reservoir is fitted to reactor through constant pressure regulator which is set at 400 psi. A back pressure regulator was fitted to reactor at gas outlet valve. Back pressure regulator is set at 390 psi. The pressure difference of 10 psi was maintained between constant pressure regulator and back pressure regulator to ensure positive flow of nitrogen. This will help in stripping of CH$_3$OH along with NH$_3$ that is formed during reaction. The reactor was then pressurized with nitrogen atmosphere at 400 psi and 25 ml methanol was added to the reactor prior to heating. The inlet valve was closed at this point keeping outlet valve open. The contents were heated to 180° C. under very slow stirring condition. After attaining the temperature the inlet valve was opened. The reaction was continued for 8 h. During this period methanol along with NH$_3$ was expelled due to the set positive pressure of nitrogen. This methanol along with dissolved NH$_3$ was collected in a trap (cooled with ice and salt mixture) connected to BPR outlet. After completion of reaction the reactor was cooled to room temperature. Reaction mixture from bomb as well as from trap was analyzed by Gas Chromatography. From GC analysis 59.1% conversion of methyl carbamate and 67.1% selectivity to DMC and 4.8% selectivity to MMC was observed in the reaction (Table 3). A part of reaction mixture was subjected to filteration and was analyzed by ICP to find the amount of Sm in solution. The ICP analysis of reaction mixture showed 0.1418 g of Sm (Table 1, entry 4).

Example 2b: 1$^{st}$ Recycle

Experiment 2a was carried out for 8 h and reactor was opened to ascertain the precipitation of catalyst. The reaction mixture was analyzed on GC and additional MC was added to make up initial MC concentration (304 mmoles). Excess methanol was removed after attaining the desired reaction temperature (180° C.) so as to adjust MC:MeOH ratio to 1:1.5. N2 and MeOH stripping at the rate 7 ml/min started and reaction was continued with precipitated catalyst following procedure mentioned in 2a for further 8 h. After 8 h reaction was stopped and reactor cooled to room temperature and reaction mixture from bomb as well as trap was analyzed by GC. GC analysis showed good reproducibility of 2a results. From GC analysis 54.4% conversion of methyl carbamate and 66.3% selectivity to DMC and 4.3% selectivity to MMC (Table 3). The ICP analysis of filtered reaction mixture showed 0.1048 g of Sm (Table 1, entry 5).

Example 2c: 2$^{nd}$ Recycle

Experiment 2b was stopped after 8 h and reaction mixture was withdrawn for GC and ICP analysis. At this point the precipitated catalyst was still present in the reaction mixture. The reaction was continued by adding MC so as to make up initial MC concentration (304 mmoles). This was followed by removal of excess methanol after attaining the desired reaction temperature (180° C.) so as to adjust MC:MeOH ratio to 1:1.5. N2 and MeOH stripping at the rate 7 ml/min started and reaction was continued with precipitated catalyst following procedure mentioned in 2a for further 8 h. After 8 h reaction was stopped and reactor cooled to room temperature and reaction mixture from bomb as well as trap was analyzed by GC. From GC analysis 47.9% conversion of methyl carbamate and 68.4% selectivity to DMC and 2.8% selectivity to MMC (Table 3). About 11% drop in MC conversion was observed after 2$^{nd}$ recycle. The ICP analysis of the filtered reaction mixture showed 0.087 g of Sm in solution (Table 1, entry 6).

Example 2d: 3$^{rd}$ Recycle

Experiment 2c was stopped after 8 h and at this point the catalyst was found to be in precipitated form in the reaction mixture. Third recycle was carried out by regenerating the catalyst. The catalyst regeneration was carried out by adding 3.975 g of triflic acid (10% methanolic solution of triflic acid) to the reaction mixture in bomb. After addition of triflic acid, catalyst precipitate dissolved and clear reaction mixture was observed. This reaction mixture was sampled out for ICP analysis which established that total Sm was restored to its original form. The ICP analysis of this reaction mixture showed 0.663 g of Sm in the reaction mixture (Table 1, entry 7) which was same to the Sm amount at the start of reaction, 0.682 g (Table 1, entry 1). The reaction was continued with regenerated catalyst following the procedure mentioned in 2a. After 8 h reaction was stopped and reactor cooled to room temperature and reaction mixture from bomb as well as trap was analyzed by GC. From GC analysis 60.9% conversion of methyl carbamate and 68.7% selectivity to DMC and 6.6% selectivity to MMC was observed. This ascertained that $Sm(CF_3SO_3)_3$ was regenerated from its precipitated form after addition of triflic acid and original MC conversion was regained (Table 3, entry 2d).

Example 2e: 4th Recycle

Experiment 2d was stopped after 8 h and at this point the catalyst was found to be in re-precipitated in the reaction mixture. Fourth recycle was carried out by regenerating the catalyst. The catalyst regeneration was carried out by adding 3.261 g of triflic acid (10% methanolic solution of triflic acid) to the reaction mixture in bomb. After addition of triflic acid, catalyst precipitate dissolved and clear reaction mixture was observed. The reaction was continued with regenerated catalyst following the procedure mentioned in 2a. After 8 h reaction was stopped and reactor cooled to room temperature and reaction mixture from bomb as well as trap was analyzed by GC. From GC analysis 63.1% conversion of methyl carbamate and 67.3% selectivity to DMC and 4.9% selectivity to MMC was observed (Table 3, entry 2e).

significantly. To reactivate the catalyst liquid stream containing precipitated catalyst was taken out from the reactor and depressurized. This stream was then filtered and 4.85 g solid catalyst was recovered. The solid catalyst was treated with 3.23 g of HNO3 (69.9% purity) to obtain 4.79 g of dark brown solid. This dark brown solid was treated with methanol and filtered to obtain 3.55 g of solid $Sm(NO3)_3$ catalyst.

This catalyst was used to ascertain its activity by carrying out standard reaction on 2 litre CSTR and presented below. The results are given in table 4.

Example 3

Methyl carbamate (MC) 228 g (304 mmol) and methanol 146 g (4562 mmol) with 3.55 g of $Sm(NO3)_3$ (catalyst regenerated from precipitate obtained in MC to DMC reaction using bubble column reactor) were charged to a 2000 ml reactor connected to a nitrogen reservoir from gas inlet valve. The reservoir is fitted to reactor through constant pressure regulator which is set at 400 psi. A back pressure regulator was fitted to reactor at gas outlet valve. Back pressure regulator is set at 390 psi. The pressure difference of 10 psi was maintained between constant pressure regulator and back pressure regulator to ensure positive flow of nitrogen. This will help in stripping of $CH_3OH$ along with $NH_3$ that is formed during reaction. The reactor was then

TABLE 3

Activity/stability study of in-situ precipitated catalyst for MC to DMC on 2 litre CSTR.

| Run no | Time (h) | Temp. °C. | MC Conv (%) | DMC sel (%) | MMC sel (%) | Wt loss (g) | observation |
|---|---|---|---|---|---|---|---|
| | | | $Sm(CF_3SO_3)_3$ catalyst | | | | |
| 2a (Std run) | 8 | 180 | 59.18 | 67.16 | 4.87 | 7.27 | Precipitate formed after 8 h |
| 2b* (1st recycle) | 8 | 180 | 54.45 | 66.33 | 4.36 | 58.31 | Precipitate retained in reaction mixture |
| 2c* (2nd recycle) | 8 | 180 | 47.91 | 68.41 | 2.80 | 23.32 | Precipitate dissolved after addition of triflic acid (3.975 g) |
| 2d* (3rd recycle) | 8 | 180 | 60.91 | 68.72 | 6.69 | 48.07 | Precipitate observed which dissolved after addition of triflic acid (dropwise addition of 10% methanolic solution of triflic acid; corresponds to 3.261 g of triflic acid) |
| 2e* (4th recycle) | 8 | 180 | 63.17 | 67.39 | 4.92 | 37.11 | Precipitate formed again |

*After every 8 h reactor was opened, reaction mixture was analyzed on GC and additional MC was added to make up initial MC concentration. Excess methanol was removed after attaining the desired reaction temperature so as to adjust MC:MeOH ratio to 1:1.5. N2 and MeOH stripping started and reaction was continued for further 8 h.

From recycle experiments it is observed that $Sm(CF_3SO_3)_3$ precipitates after bubbling of $NH_3$ in initial reaction mixture. This precipitate could be dissolved initially by $N_2$ stripping at 90° C. but the nature of precipitate changes after reaction and this precipitate could not be re-dissolved even after prolonged N2 bubbling at reflux temperature. But on addition of triflic acid precipitate dissolves and original activity was regained. This indicates that precipitated catalyst is active in-situ with total amount of samarium distributed in solution and in precipitated catalyst without any loss in total Sm content.

Example 3: Catalyst Regeneration from Bubble Column in Bench Scale Set Up and Recycle on 2 Litre CSTR During the MC to DMC reaction in bubble column the $Sm(NO3)_3$ catalyst is precipitated and its activity drops pressurized with nitrogen atmosphere at 400 psi and 25 ml methanol was added to the reactor prior to heating. The inlet valve was closed at this point keeping outlet valve open. The contents were heated to 180° C. under very slow stirring condition. After attaining the temperature the inlet valve was opened. The reaction was continued for 8 h. During this period methanol along with $NH_3$ was expelled due to the set positive pressure of nitrogen. This methanol along with dissolved $NH_3$ was collected in a trap (cooled with ice and salt mixture) connected to BPR outlet. After completion of reaction the reactor was cooled to room temperature. Reaction mixture from bomb as well as from trap was analyzed by Gas Chromatography. From GC analysis 52.2% conversion of methyl carbamate and 63.4% selectivity to DMC and 4.2% selectivity to MMC was observed in the reaction (Table 4).

The regained activity of regenerated catalyst in above example shows that catalyst can be recycled in discontinuous mode also.

TABLE 4

DMC synthesis using Sm(NO₃)₃ regenerated from precipitated catalyst

| Entry | Catalyst | Time (h) | Temp (° C.) | MC Conv (%) | DMC Sel (%) | MMC Sel (%) |
|---|---|---|---|---|---|---|
| 1 | Sm(NO3)3 regenerated from precipitate recovered from bubble column reactor | 8 | 180 | 52.2 | 63.4 | 4.2 |

Example 4: Detailed Process for Catalyst Recycle and Regeneration in a Tubular Reactor Dissolved solution of urea in alcohol is stored in Urea+Alcohol feed vessel (1) which is pumped by pump (31) to Tubular reactor (3). Alcohol is stored in vessel (2) and is vaporized/superheated in heater (5). This superheated alcohol (stream 20) can be used as a stripping agent. Ammonia generated during Urea alcoholysis is removed in stripper (4) by stripping with superheated alcohol/suitable stripping agent and remaining solution (urea+alkyl carbamate+alcohol, stream –19) is sent to Dialkyl carbonate reactor (11) with the help of pump (9). Overhead stream of stripper (4) is then cooled down in cooler (6) and flashed in vessel (7). Overhead stream (22) containing ammonia can then be sent to scrubbing system. Liquid phase from vessel (7) is temporarily stored in vessel (8) only to be pumped by pump (10) to the Dialkyl carbonate reactor (11) as alcohol reflux (stream 23). Other stream containing superheated alcohol (20) is sent to the Dialkyl carbonate reactor (11) as well. Bottom product from this reactor is stored in bottom product storage vessel (16) and overhead stream is passed through condenser (12), flash vessel (13) to be eventually stored in top product storage vessel (15). Some part of the top product is recycled back to the reactor by pump (14).

The catalyst regeneration and recovery loop is shown with dotted line. The stream containing reactor contents (stream 24) is taken from reactor and is optionally treated with ammonia (stream 25) in filtration/precipitation vessel (17). The stream containing liquid phase (stream 26) is sent back to the reactor and stream containing mainly solid phase slurry (stream 27) is sent to the Regeneration vessel (18). Here the slurry is treated with appropriate acid (stream 28) to regenerate the catalyst and the regenerated catalyst stream (stream 30) is then sent back to the reactor (11). From the liquid phase a purge stream (stream 29) is taken to avoid accumulation of unwanted products in reactor which are treated appropriately.

ADVANTAGES OF INVENTION

The main advantage of the process developed is that the method is simple and can be conveniently integrated with the overall manufacturing process.

The activity of the regenerated catalyst is comparable to the fresh catalyst.

The processes for regeneration and recovery of catalysts for the process of synthesis of dialkyl carbonates are conveniently integrated within the overall flow sheets of manufacturing dialkyl carbonates.

The process offers a convenient way to establish and maintain consistent activity and selectivity towards desired dialkyl carbonates.

We claim:

1. A process for recovery and regeneration of a deactivated catalyst comprising the steps of:
   (a) adding a reaction mixture including an alkyl carbamate, an alcohol and a rare earth metal salt including a lanthanide series element in a reactor;
   (b) partially removing the reaction mixture of step (a) from a bottom of the reactor;
   (c) separating the deactivated catalyst from the partially removed reaction mixture of step (b);
   (d) dissolving the deactivated catalyst in acid;
   (e) recovering a regenerated active catalyst from the dissolving step; and
   (f) directly sending the regenerated active catalyst of step (e) to a reactor for synthesizing dialkyl carbonate.

2. The process as claimed in claim 1, further comprising adding ammonia to the partially removed reaction mixture of step (b) in a pressure range of 1 to 25 bar and a temperature ranging from 60 to 200° C. to precipitate the deactivated catalyst.

3. The process as claimed in claim 1, wherein said dialkyl carbonate is selected from di methyl carbonate, di ethyl carbonate, di propyl carbonate, and di butyl carbonate.

4. The process as claimed in claim 1, wherein said lanthanide series element is selected from Samarium (Sm), Cerium (Ce), Lanthanum (La), Neodymium (Nd), Ytterbium (Yb), Europium (Eu) and Gadolinium (Gd).

5. The process as claimed in claim 1, wherein said salt is selected from methane sulphonate, triflate, nitrate, chloride and para toluene sulphonate.

6. The process as claimed in claim 1, wherein said dialkyl carbonate is di methyl carbonate and said rare earth metal-salt is samanum trifluoromethanesulfonate.

7. The process as claimed in claim 1, wherein said acid is selected from methane sulphonic acid, trifluoromethanesulfonic acid, nitric acid, para toluene sulfonic acid and hydrochloric acid.

8. A process consisting of:
   (a) providing a reaction mixture including an alkyl carbamate, an alcohol and a rare earth metal salt including a lanthanide series element in a reactor;
   (b) partially removing the reaction mixture of step (a) from a bottom of the reactor;
   (c) separating a deactivated catalyst from the partially removed reaction mixture of step (b);
   (d) dissolving the deactivated catalyst in acid;
   (e) recovering a regenerated active catalyst from the dissolved deactivated catalyst of step (d); and
   (f) directly sending the regenerated active catalyst of step (e) to a reactor for synthesizing dialkyl carbonate.

* * * * *